United States Patent [19]

Servello

[11] Patent Number: 4,969,454
[45] Date of Patent: Nov. 13, 1990

[54] EMERGENCY PERCUTANEOUS CRICOTHYROTOMY DEVICE

[76] Inventor: Anthony J. Servello, 435 Old Hickory Dr., Pittsburgh, Pa. 15235

[21] Appl. No.: 885,794

[22] Filed: Jul. 14, 1986

Related U.S. Application Data

[63] Continuation of Ser. No. 667,860, Nov. 2, 1984.

[51] Int. Cl.$^5$ ............................................. A61B 17/32
[52] U.S. Cl. ............................................... 606/185
[58] Field of Search ...................... 128/305.3, 305, 329

[56] References Cited

U.S. PATENT DOCUMENTS

| | | | |
|---|---|---|---|
| 300,285 | 6/1884 | Russell | 128/305.3 |
| 2,991,787 | 7/1961 | Shelden et al. | 128/305.3 |
| 3,182,663 | 5/1965 | Abelson | 128/305.3 |
| 3,384,087 | 5/1968 | Brummelkamp | 128/305.3 |
| 3,511,243 | 5/1970 | Toy | 128/305.3 |
| 3,643,649 | 2/1972 | Amato | 128/305.3 |
| 3,688,773 | 9/1972 | Weiss | 128/305.3 |
| 3,916,903 | 11/1975 | Pozzi | 128/305.3 |
| 4,182,337 | 1/1980 | Nickson | 128/305.3 |
| 4,331,138 | 5/1982 | Jessen | 128/305.3 |
| 4,471,778 | 9/1984 | Toye | 128/305.3 |

FOREIGN PATENT DOCUMENTS 2607935  9/1976  Fed. Rep. of Germany ... 128/305.3

Primary Examiner—Kenneth J. Dorner
Assistant Examiner—J. Hakomaki
Attorney, Agent, or Firm—Reed Smith Shaw & McClay

[57] ABSTRACT

A cricothyrotomy device for emergency use includes a syringe with a removable plunger, a needle or hollow metal stylet which is mountable on the syringe, a catheter also attachable to the syringe and coaxial with the stylet, and an adaptor to fit when the syringe is in place to provide for ventilation access to the lumen of the patient.

4 Claims, 2 Drawing Sheets

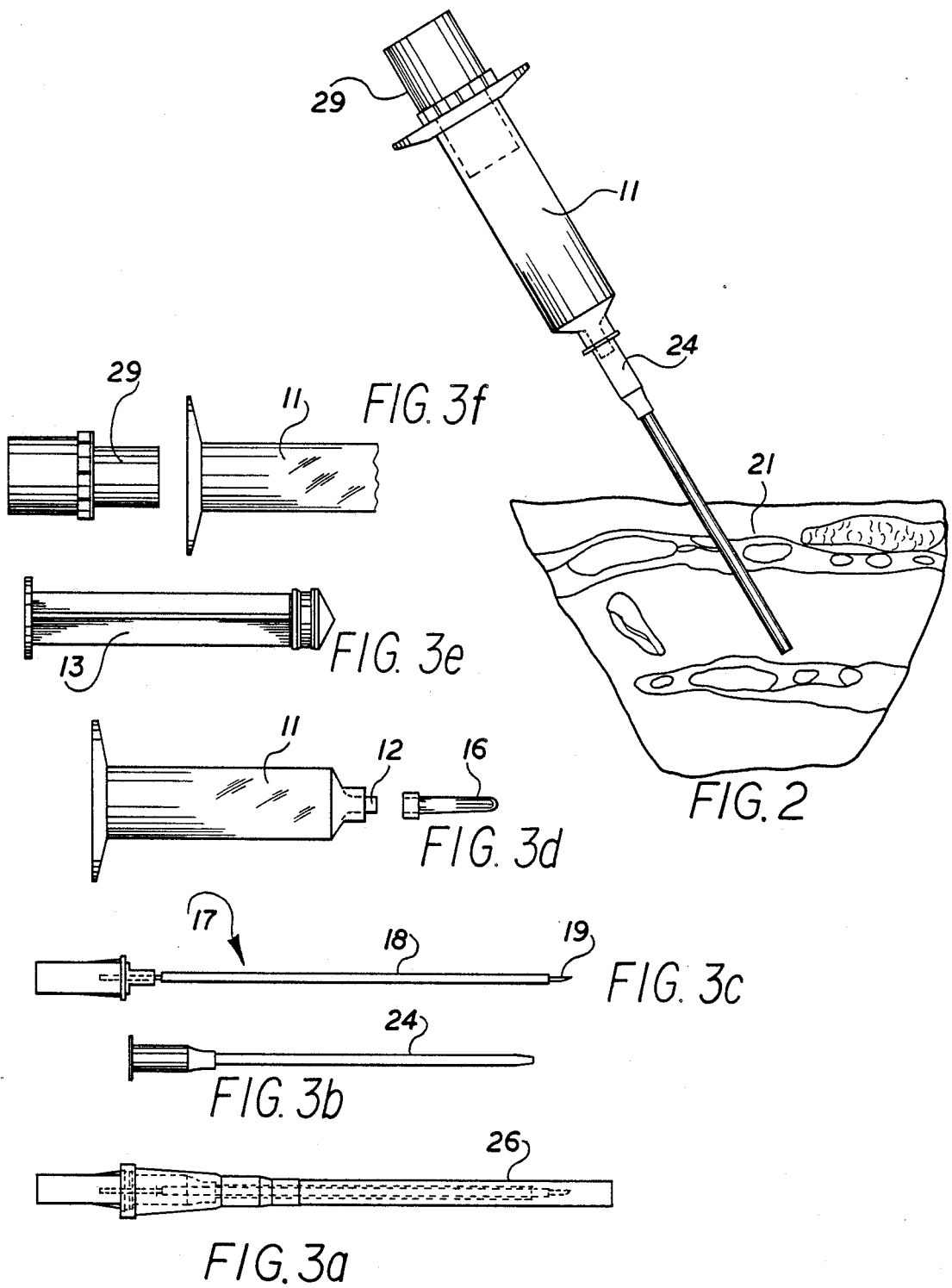

EMERGENCY PERCUTANEOUS CRICOTHYROTOMY DEVICE

This is a continuation of co-pending application Ser. No. 667,860 filed on Nov. 2, 1984.

FIELD OF THE INVENTION

The present invention relates to a device for performing emergency cricothyrotomies or tracheotomies, and, in particular, to a highly portable means for performing tracheotomies outside of the hospital and in hospital where conventional techniques fail to establish an airway in a patient.

BACKGROUND OF THE INVENTION

It is not uncommon for a person to lose the use of an airway passage by virtue of having a piece of food or the like lodge in the passageway or a constriction caused by trauma. Since a restriction in the air passageway to the lungs can be a life threatening situation, particularly where the total supply of air is stopped, quick emergency attention is required by that person. In a number of these situations, such as in choking, it is possible to remove the obstruction in a nonevasive manner. However in many situations it is necessary to perform percutaneous transtracheal ventilation or tracheotomy.

A number of devices have been proposed to perform emergency laryngeal-tracheal operations (cricothyrostomy). For example, U.S. Pat. Nos. 3,906,956; 4,331,138; 3,476,113; and 4,003,381 disclose devices which facilitate the creation of an airway into the lumen of the trachea. However, a disadvantage of many of these devices is that they require the skill of a surgeon to insert. Additionally, the diameter of the device is such that the opening created is quite large and if not done precisely right, will damage organs and tissue surrounding the opening.

More recently, cricothyroidotomy instruments have been proposed that overcome a number of disadvantages of the prior art devices. An example of these devices are disclosed in U.S. Pat. Nos. 4,364,391 and 4,438,768. Basically, these devices provide a needle like means for connection to a ventilator used in the operating room, see also Scuderi et al. "Emergency Percutaneous Transtracheal Ventilation During Anesthesia Using Readily Available Equipment" Vol. 61, No. 10 Oct. 82, *ANESTHESIA AND ANALGESIA*. While these newer devices overcome many of the problems mentioned, they are not useful for performing emergency cricothyroidotomies in the field, especially by nonsurgical personnel.

Accordingly, it is an object of the present invention to provide an emergency percutaneous cricothyrotomy device which is selfcontained and capable of penetrating the cricothyroid membrane into the tracheal lumen and provide adequate emergency ventilation. It is a further object of the present invention to provide a device by which a cricothyrotomy can be performed by a paramedic, medical or relatively undertrained medical person.

SUMMARY OF THE INVENTION

Generally, the present invention comprises a syringe having an elongated needle attached thereto and consisting of a beveled end and hollow stylett. A teflon catheter is positioned over the stylet and also is connected to the syringe. An insertable adapter is provided to connect the other end of the syringe to a ventilating device after the catheter is inserted amd the syringe plunger removed.

The present invention is specifically designed as a temporary means of ventilation support in an acute airway crisis. It can be used throughout the laryngeal-tracheal region, but is preferably used in the cricoid-thyro space. The preferred area is easy to locate in all types of patients with palpitations of the neck area. Moreover, in the cricothyroid space there are less critical organs or structures thereby rendering the procedure safer.

The invention provides a safe and easy method for performing a percutaneous transtracheal ventilation. The syringe needle with the catheter over the outer portion of the stylet is inserted into the cricoid-thyro region. The bevelled end of the stylet penetrates the trachea into the lumen. Reaching the lumen is readily apparent by withdrawing the plunger and having aspiration and injection of air, and viewing the contents if any drawn into the syringe. Once it is established that the stylet is within the lumen, the catheter is inserted into the opening and stylet needle withdrawn and immediately removed from the syringe. The catheter is then reconnected to the syringe and the plunger removed. If necessary, the adapter is inserted into the syringe end and a ventilation device attached thereto. The procedure is easy and safe. It quickly establishes a temporary air passageway without the possibility of passing through the posterior wall into the esophagus. Other advantages of the present invention will become apparent from a perusal of the following detailed description of a presently preferred embodiment taken in connection with the accompanying drawings.

BRIEF DESCRIPTION OF THE DRAWINGS

FIG. 2 is a sectional elevation of device after the needle and plunger of the syringe have been removed and and only the catheter and adapter are attached to the syringe; and FIGS. 3(a)-(f) show the various component parts of the present invention,

PRESENTLY PREFERRED EMBODIMENT

Figure 1:
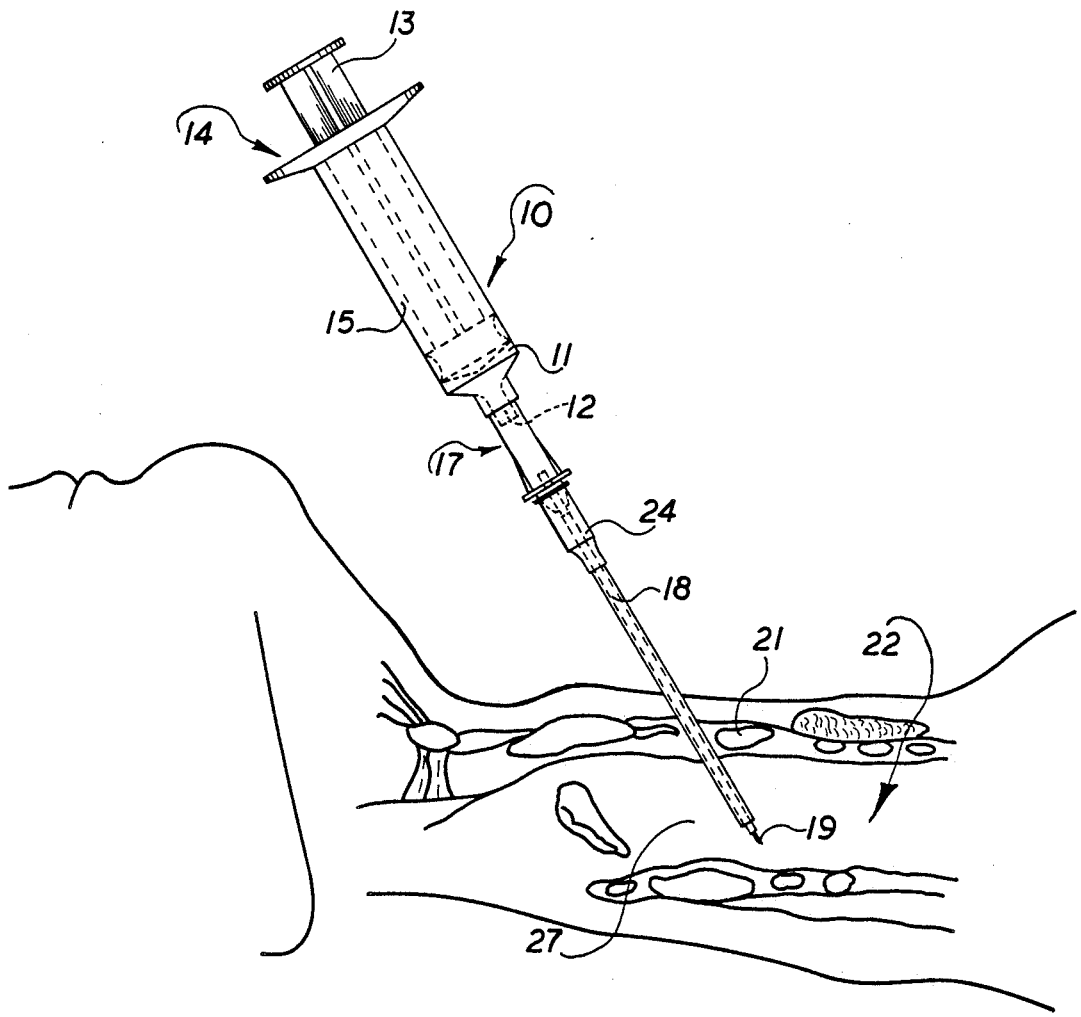
FIG. 1 is a side elevation in section showing the cricothyrotomy device of the present invention penetrating the cricothyroid membrane in an acutely obstructed patient.

With reference to FIGS. 1 and 3, cricothyrotometric device 10 of the present invention comprise a syringe 11 having a luer type end 12. Syringe 11 also includes movable plunger 13 which is capable of movement along the cylindrical length of syringe 11. Plunger 12 is also removable from the syringe at end 14. At the other end 16, needle 17 is attached to the luer type fitting 12 of the syringe.

Needle 17 comprises a hollow metal stylet 18 having a sharp bevelled end 19. Bevelled end 19 is adapted to penetrate the thick cricothyroid cartilage 21 of trachea 22. Positioned over stylet 18 is catheter 24, preferably made from teflon. As can be seen from FIG. 1, catheter 24 shorter in length than stylet 18, and includes attachment means 26 to fit onto syringe 11 and fitting 12.

As shown in FIG. 1, needle 17 penetrates the cartilage 21, catheter 24 is inserted into the opening by pushing the syringe further into the lumen area 27. However, to affirm that the needle is in the lumen area prior to advancing the catheter, plunger 13 can be withdrawn to determine the nature of the material at the bevelled end 19 of the stylet. If little or no blood is drawn into chamber 15 of the syringe and there is aspiration of air, it is safe to push the syringe the short distance to insert the catheter.

After catheter 24 has been inserted into the lumen 27, syringe 11 and needle 17 are withdrawn from within the catheter. Needle 17 is removed from syringe 11 and syringe 11 is reattached to catheter 24. Also at this time, plunger 13 is removed from chamber 15 and adapter 29 is inserted into end 14 of the syringe, as shown in FIG. 2.

While not shown in FIG. 2, adapter 29 connects to standard ventilating equipment typically found on emergency resuce or medical vehicles. Adapter 29 also may be connected to anesthesia machines located in hospital operating room. Even if such ventilating equipment is not readily available, the diameter of catheter 24, which is preferably about 2.8 mm, is sufficient to permit the person breathe through it. If spontaneous breathing does not occur, air may be blown directly into the lungs through adapter 29 by rescue personnnel.

As shown in FIGS. 3(a)-(f), the various components of the present invention can be packaged in a convenient kit of relatively small size, i.e., all of the components necessary to the device are themselves small so that the device can be packaged in pre-sterilited packages for immediate emergency use. It is also to be understood that in such packaging with the device can be sutures and germicidal solution. Since it is preferable that all of the components are disposable, the present invention can be made from relatively inexpensive materials. In addition to the components mentioned above, it is desirable to include a cover 16 for luer end 12 of syringe 11 and a cover 26 for needle 17 and catheter 24, as shown in 3(d) and 3(a), respectively.

Consequently, the present invention provides a safe, easy to use, and inexpensive cricothyrotomy instrument which is made up of pre-sterilizable components that are easy to assemble without the need for special tools or equipment. With the present invention a percutaneous transtracheal air passage can be safely and quickly established by nonsurgical personnel.

While a presently preferred embodiment of the invention has been shown and described in particularity, it may be otherwise embodied within the scope of the appended claims.

What is claimed is:

1. A percutaneous cricothyrotomic device for emergency use comprising:
   a. A syringe having a removable plunger and luer-type fitting at one end and an opening at the other end through which said plunger may be removed, said syringe having inner walls;
   b. a needle comprising a hollow metal stylet having a sharp bevelled end and with the other end being removably mounted to said luer-type fitting;
   c. a catheter removably attached to and coextensively positioned over said stylet for a substantial portion of the length of said stylet, and having an inner diameter slightly larger than the outer diameter of said stylet so as to slideably fit thereover; and
   d. an adoptor means for allowing a ventilating means to be connected to the end of the syringe after said plunger has been removed, said adaptor means includes a first elongated cylindrical member adapted to slidingly engage the inner walls of the syringe and a second elongated cylindrical member connected to said first member and having a diameter slightly larger than said first member adapted to securely receive the ventilating means.

2. A percutaneous cricothyrotomic device as claimed in claim 1 wherein said syringe fitting is a luer-type and said catheter is made from Teflon plastic.

3. A percutaneous cricothyrotomic device as claimed in claim 1, wherein said catheter is adapted to fit on luer-type fitting after said needle is removed.

4. A percutaneous cricothyrotomic sterilized kit having a plurality of components adapted to fit together to provide a cricothyrotomic device, said components comprising
   a. a syringe having a removable plunger and a luer-type end having a removal cap attached thereto and an opening at the other end through which said plunger may be removed, said syringe having inner walls;
   b. a needle comprising a hollow stylet and a bevelled end and an end adapted to fit on the luer-type end of said syringe;
   c. a catheter having an end adapted to fit on said syringe when the needle is either on or off said syringe, and having a length slightly shorter than said needle, said catheter having an inner diameter slightly larger than the outer diameter of said needle so as to slideably fit over said needle;
   d. an adaptor means for allowing a ventilating means to be connected to the end of the syringe through which said plunger may be removed, said adaptor means includes a first elongated cylindrical member adapted to slidingly engage the inner walls of the syringe and a second elongated cylindrical member connected to said first member and having a diameter slightly larger than said first member adapted to securely receive the ventilating means;
   e. means for covering said needle and catheter when said needle and catheter are positioned together; and
   f. a sterilized sealed package means for containing said syringe, needle, catheter, adaptor with the associated covers in place.

* * * * *